United States Patent [19]
Dreyfus

[11] Patent Number: 5,854,486
[45] Date of Patent: Dec. 29, 1998

[54] METHOD AND APPARATUS FOR MALDI MASS SPECTROMETRY

[75] Inventor: Russell W. Dreyfus, Madrid, Spain

[73] Assignee: R. T. Hodgson, Ossining, N.Y.

[21] Appl. No.: 775,016

[22] Filed: Dec. 27, 1996

[51] Int. Cl.⁶ ................................................ H01J 44/04

[52] U.S. Cl. .......................................................... 250/288

[58] Field of Search ................................. 250/288, 281, 250/282; 436/173

[56] References Cited

U.S. PATENT DOCUMENTS 4,920,264  4/1990  Becker ...................................... 250/288

*Primary Examiner*—Kiet T. Nguyen
*Attorney, Agent, or Firm*—R. T. Hodgson

[57] ABSTRACT

A thin uniform film of matrix material is deposited from the gas phase on to a substrate for use in Matrix Assisted Laser Desorption and Ionization (MALDI) spectroscopy. The thin uniform film of material may be overcoated with another film of material which has a higher vapor pressure than the matrix material to prevent the matrix material from evaporating during storage and during substantial time in the vacuum environment of the mass spectrometer.

7 Claims, 3 Drawing Sheets

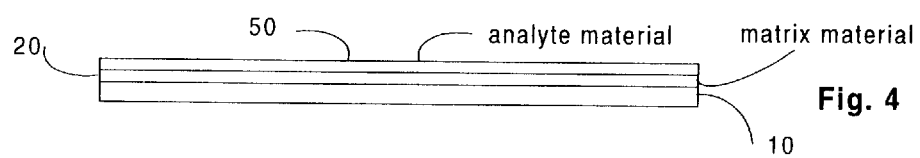
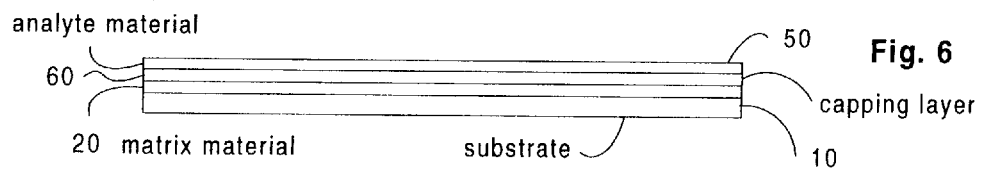
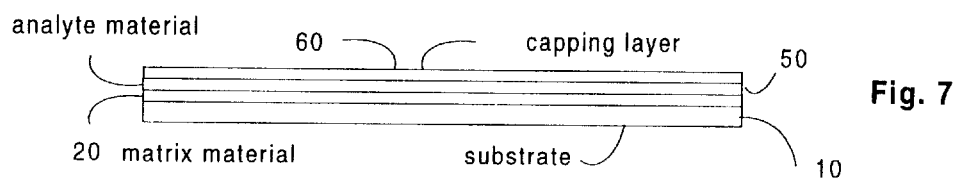

Scanning Electron Micrograph of a Coumarin 120 film formed by sublimation

METHOD AND APPARATUS FOR MALDI MASS SPECTROMETRY

FIELD OF THE INVENTION

The field of the invention is the field of mass spectrometry, and in particular the field of sample preparation for samples which are introduced into a mass spectrometer.

BACKGROUND OF THE INVENTION

Mass spectroscopy has been used for many years to determine the mass and thus identify sample compositions by relating the mass of atoms and molecules produced from the samples to the composition of the sample. Typically, the atoms and molecules of interest are ionized so that the particles produced from the sample may be moved and steered through the mass spectrometer apparatus and then detected in a detector. The atoms and molecules of the sample have often been ionized by electron collision. However, the electron collision has the disadvantage that molecules are broken apart, or "cracked" in the collision, and the resulting mass spectrum must be interpreted in the light of the "cracking pattern" which results for electron collision with a particular molecule. For very large molecules, this process becomes very tedious and can not be used to determine mixtures containing a significant number of different molecules.

A method of avoiding the "cracking" problem is the Matrix Assisted Laser Desorption and Ionization (MALDI) method of mass spectrometry. A sample to be measured is mixed with another material, called a matrix, and deposited on a substrate. A pulsed laser beam is then used to desorb some of the matrix material and the sample, and if the correct laser beam fluence is used, some of the resultant sample material desorbed from the substrate will be ionized and can be introduced into a mass spectrometer. Articles reviewing work in this field are "Desorption methods in mass spectrometry", by Bo. U. R. Sundqvist, Int. J. Mass Spectrometry and Ion Processes, 118/119, 265–287 (1992) and Matrix-assisted laser desorption and ionization", by J. A. Carroll and R. C. Beavis, chapter 7 in Laser Desorption and Ablation in the series Experimental Methods in the Physical Sciences, Editors J. C. Miller and R. F. Haglund, Jr., available off the internet at http//128.122.10.3/MALDI/ChemPhysMan.htm.

The matrix material for MALDI is typically a material which has a relatively high vapor pressure, and can be evaporated from the substrate easily when the material is heated by the laser beam.

The matrix material is typically dissolved in a volatile solvent, and the substance to be investigated is added to the mix in molecular ratios of about 1:1000 of matrix material. The mixture is then dropped or sprayed on a substrate and allowed to dry. The matrix material forms crystals as the volatile solvent evaporates, and the growing crystals entrap the molecules of the substance to be investigate so that the substance is incorporated into the resultant solid layer. The crystals of the matrix material grow from random seeding centers on the substrate to form a rough film which does not entirely cover the substrate.

A number of problems with the MALDI technique have been investigated. For example, the substance to be investigated may dissolve easily only in a non volatile solvent, and the residue of the solvent prevents the material from properly desorbing and ionizing. This problem has been addressed by Xiang and Beavis, Rapid Comun. Mass Spectrom. 8, 199–204, (1994). The authors deposit a thick film of pure matrix crystals on to the substrate, then scrub the film mechanically to align the crystals with the substrate so that the crystals adhere well to the substrate. The mixture of the substance to be investigated and the matrix material is then deposited on the well adhered crystal matrix material layer, and crystals of the matrix material, which incorporate the substance to be investigated, grow as a second layer on the "seed bed" of the prepared matrix material. The second layer mixture of matrix and substance can then be washed to remove involatile solvent material without removing the mixture in the second layer or the first layer from the substrate. This method forms a thick and rough film, and the original matrix material layer does not cover the substrate uniformly, but leaves about 20% open area.

A problem with the above cited works is that the matrix film does not cover the entire surface and is too thick and too non-uniform. For quantitative measurements, different amounts of material will be removed from the surface for each laser shot, depending on the details of the surface preparation and the particular area of the surface illuminated by the laser.

A self assembled monomolecular layer of matrix material can be deposited on the substrate as detailed in an article by Mouradian et al. in J. Am. Chem. Soc. 118, 8639–8645 (1996). A covalent bond is formed between the molecules of the matrix material and a gold coating on the substrate. The matrix material is very thin, however, and very few shots of the laser deplete all the matrix material.

An unrecognized problem with MALDI is the problem of stability of the materials. High vapor pressure matrix materials are preferred since the material can be desorbed from the substrate with less laser fluence. The low laser fluence damages the molecules to be investigated less than higher fluence needed to evaporate lower vapor pressure materials. However, the high vapor pressure, thin matrix material loses material by sublimation when stored at room temperature, or kept in the vacuum system of the mass spectrometer for an appreciable length of time.

The contents of the articles cited herein are hereby included in their entirety by reference.

OBJECTS OF THE INVENTION

It is an object of the invention to provide a substrate covered with a uniform, pinhole free film of matrix material of sufficient thickness for MALDI mass spectrometry.

It is an object of the invention to provide a method of producing a substrate covered with a pinhole free film of uniform thickness matrix material for MALDI mass spectrometry.

It is an object of the invention to provide a substrate covered with a uniform, pinhole free film of matrix material for MALDI mass spectrometry, the matrix material having a long shelf life and an adequate stability in a vacuum system.

SUMMARY OF THE INVENTION

A thin, uniform film of matrix material is deposited on a substrate by sublimation of the solid matrix material or by other vapor deposition methods. A second uniform layer having a much higher sublimation temperature may be deposited on the matrix material layer to protect the matrix material layer from sublimation during storage or during the time the matrix material is kept in a vacuum system of a mass spectrometer.

BRIEF DESCRIPTION OF THE DRAWINGS

FIG. 4. A sketch of a layer of matrix material deposited on a substrate by the method of the invention, with a layer of analyte material deposited on the layer of matrix material FIG. 5. A sketch of a layer of matrix material of the invention, with an innovative capping layer deposited on the layer of matrix material.

FIG. 6. A sketch of a layer of matrix material of the invention, with an innovative capping layer deposited on the layer of matrix material, and a layer of analyte material deposited on the capping layer.

FIG. 7. A sketch of a layer of matrix material of the invention, with a layer of analyte material deposited on the layer of matrix material, and an innovative capping layer deposited on the layer of analyte material.

DETAILED DESCRIPTION OF THE INVENTION

Figure 1:
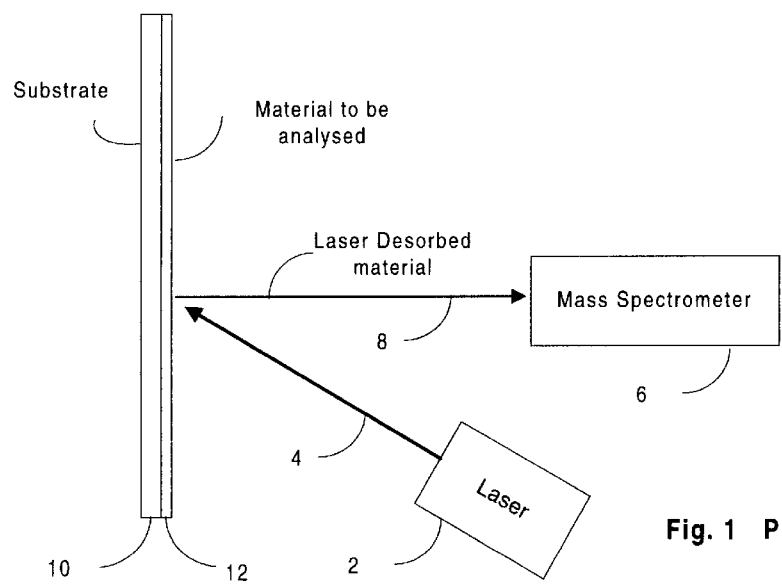
FIG. 1. A sketch of a prior art MALDI mass spectrometry set up.

FIG. 1 shows a sketch of the prior art MALDI mass spectrometry method. A substrate 10 is prepared by depositing a layer 12 of matrix material intermixed with a substance to be analyzed on to the surface. A laser 2 is used to produce a pulsed laser beam 4 which impinges on to the layer 12. Material 8 is desorbed from the surface, and progresses towards a mass spectrometer 6, where the material 8 is mass analyzed to give a mass spectrum.

An ultraviolet laser 2 is conventionally used in MALDI mass spectrometry, but the use of other pulsed sources of energy such as infrared or visible light emitting diodes or injection laser diodes or other sources of localized heating such as electron beams are anticipated by the inventor.

The material to be analyzed 12 is usually a mixture of a matrix material and a few parts per thousand of an analyte material. The matrix material is usually a material which has a very high absorption coefficient for laser light and a low vaporization temperature. These characteristics lead to a high temperature in a very shallow depth of the layer 12 of the material to be analyzed for a low laser fluence of the laser beam 4. The high temperature and low vaporization temperature of the matrix material lead to efficient desorption of a thin layer of heated material on the surface of layer 12.

The analyte material preferably does not absorb the light from the laser beam 4. The analyte material is preferably carried into the vapor phase so fast that the analyte material is not hot enough for a long enough time to break apart. The vapor of the matrix material and the analyte material cools rapidly by expansion. The molecules of the analyte material are preferably charged by transfer of a hydrogen ion between an analyte molecule and a matrix molecule, but the exact charging mechanism is not clear at this time.

The mass spectrometer 6 is typically a time of flight (TOF) mass spectrometer to make use of the pulsed nature of the analyte source. However, other mass spectrometer types such as quadrapole mass spectrometers and ion trap mass spectrometers as are well known in the art could also be used.

Figure 2:
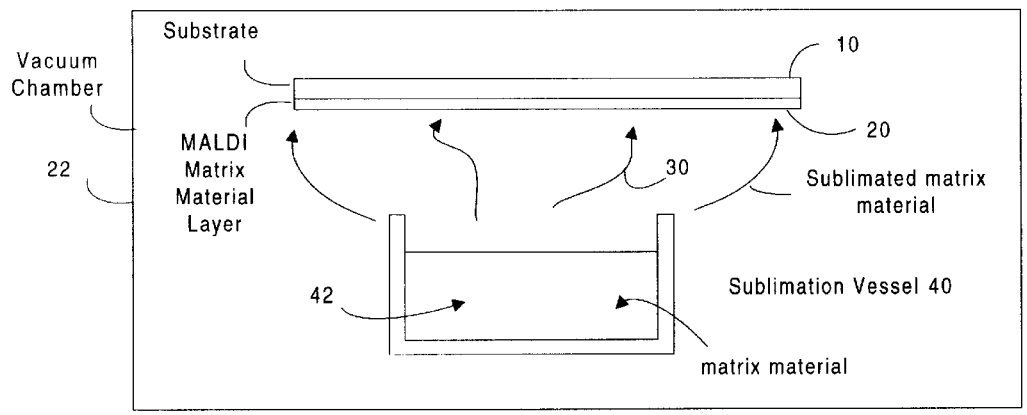
FIG. 2. A sketch of the most preferred method of depositing a thin, pinhole free layer of matrix material on to a substrate of the invention.

FIG. 2 shows a sketch of the method of preparing a thin, pinhole free film of matrix material for use in MALDI spectroscopy. A matrix material 42 is contained in a sublimation vessel 40 and held at a determined temperature $T_1$. A substrate 10 is held facing the vessel 40. The temperature of the substrate 10 is less than the temperature $T_1$. The matrix material 42 sublimes or evaporates, and the molecules 30 of the sublimated matrix material move across the space between the vessel 40 to the substrate 10 to condense as a layer 20 on the substrate 10. While the sublimation may take place in an atmosphere of suitable gas, the space between the vessel 40 and the substrate 10 is preferably evacuated to produce more uniform films. A vacuum chamber 22 may be conveniently used for this purpose. The pressure in the space between the vessel 40 and the substrate 10 is generally about $10^{-4}$ torr, which is generally determined by the vapor pressure of the matrix material itself. At $10^{-4}$ torr, the molecules of the matrix material fly directly from the solid matrix material in the vessel 40 to the substrate 10 with low probability of collision with other matrix molecules or with residual molecules of atmospheric gas.

If the substrate is at sufficiently low temperature, the molecules of the matrix material 30 are not very mobile on the surface of the substrate 10, and the molecules of the matrix material agglomerate to form a high surface density of very small crystals of the matrix material on the substrate. The crystals of the matrix material act as seeds, and the seed crystals grow until they touch each other and form a uniform film 20. Depending on the temperature of the substrate, the seeding density can be very high, and the seed crystals will be very small when they touch each other and form a continuous film. Thus a very thin film 20 of matrix material may be grown without pinholes. The film 20 is preferably thicker than 1 nm, more preferably thicker than 10 nm, and most preferably thicker than 100 nm which allows efficient use of the laser light to desorb the film. As the films grown thicker than 1 micron, the surface becomes rougher. However, the method may still be used to produce films 20 of 10 microns and thicker. The thickness uniformity of the film across the area to be illuminated by laser beam 4 is preferably more uniform than +/-50%, and most preferably more uniform than +/-10% of the average film thickness. The area of substrate 10 covered by layer 20 of matrix material has preferably less than 10% of the area of the layer 20 across the area to be illuminated by laser beam 4 with pinholes in layer 20, and most preferably less than 1% of the area with pinholes in layer 20.

As the temperature of the substrate is lowered, for example by contacting the substrate 10 to a cryogenic cooler, molecules deposited from the vapor phase will not have sufficient energy to crystallize, and the film 20 will be amorphous. In this case, even thinner continuous films are produced. Such amorphous films are very smooth and uniform. Depending on the matrix material chosen, the amorphous films may or may not crystalize as the film temperature is raised from the deposition temperature to room temperature.

Analyte material may be added to the matrix material 42 in the sublimation vessel 40 to produce a single film 20. However, higher temperatures $T_1$ may adversely affect the analyte material. Also, the rate of deposition of the matrix material and the analyte material may be different than the ratio of matrix material and analyte material in the vessel 40.

Figure 3:
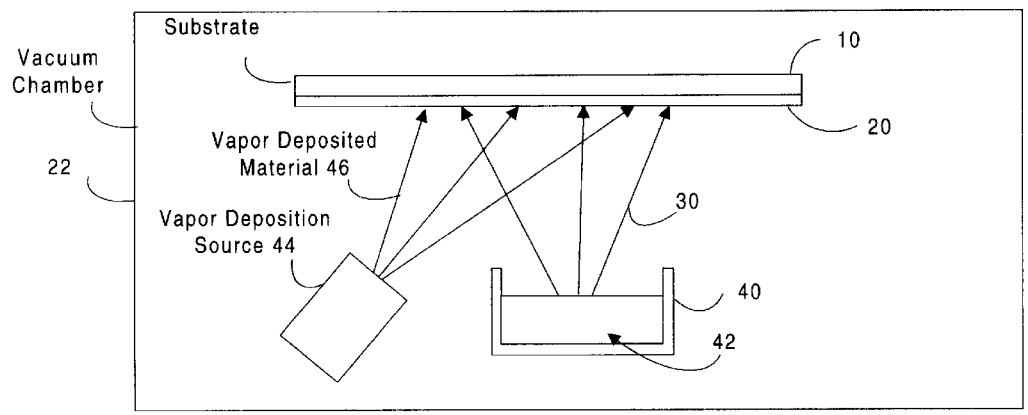
FIG. 3. A sketch of a preferred method of depositing a uniform thin, pinhole free layer of matrix material a matrix material intermixed with another material.

In this case, analyte material may be added to the matrix material in layer 20 by simultaneous vapor deposition of vapor 46 containing the analyte material at an appropriate rate from another vapor source 44 as shown in FIG. 3.

Other methods of introducing matrix molecules on to the surface of a substrate from the vapor phase include, but are not limited to, ion, electron and laser beam vaporization or sputtering sources.

FIG. 4 shows a structure where a layer of matrix material 20 deposited on a substrate 10 has a layer of analyte material 50 deposited on the layer of matrix material 20. The underlying matrix material 20 controls the growth of the crystals of the overlying analyte material or mixture of analyte and matrix material by providing a very uniform seed bed of crystals which are well adhered to the substrate 10. The uniform seed bed avoids the problem of the prior art of random seeding and growth which provides rough surfaces having pinholes.

The analyte material 50 may be deposited on the matrix material of layer 20 by a number of techniques. The easiest of such techniques is merely to drop a drop of solution containing the analyte material, a volatile solvent, and optionally matrix material on the surface of the layer 20 and to allow the volatile component of the solution to evaporate. The analyte molecules may be held by the molecules of the matrix layer 20, or may be held by matrix material which grows from the solution on to the matrix material of layer 20, or the solution may dissolve some of the layer 20, and the analyte material may incorporate into the crystal as the matrix material regrows on the remaining crystalline material of layer 20 during the evaporation of the volatile solvent.. This technique is particularly valuable when the solution contains a non-volatile solvent, as is often necessary to dissolve some analyte materials. The analyte becomes trapped in the matrix molecules which grow on the material of layer 20, and the non-volatile solvent may be washed away without washing away the analyte molecules or the well adhered molecules of layer 20.

Analyte material may be dissolved in a solvent which does not dissolve the material of the matrix layer 20, and a drop of such a solution placed on the matrix layer 20. The analyte material may then adhere to the matrix material of layer 20, and the remaining involatile solvent may be washed away with a volatile solvent which will not dissolve the matrix layer 20.

Another technique for producing layer 50 is to spray a solution of analyte and solvent from a nebulizer on to the matrix material 20 If the solvent is volatile, it will evaporate leaving the analyte molecules on the surface of the matrix material 20. If the analyte is mixed in the solution with matrix molecules, the solution sprayed on the surface will form a film, and the matrix molecules will grow on the template formed by matrix molecules of the layer 20 and entrap the analyte molecules in the growing layer 50. Care must be taken to avoid dissolving all the matrix material of layer 20.

Another technique for depositing a layer 50 of analyte molecules on the matrix layer 20 is to use an electrospray device to spray a solution of analyte molecules and a volatile solvent on to layer 50. Once again, the layer 50 may contain both analyte molecules and matrix molecules admixed in the correct ratio.

Another technique for depositing a layer 50 of analyte molecules on the matrix layer 20 is to use a vapor deposition technique such as sublimation, or such as laser deposition or ion beam or electron beam heating and deposition.

FIG. 5 shows an innovative structure where a layer of matrix material 20 deposited on a substrate 10 has a capping layer 60 deposited on the layer of matrix material 20. The capping material 60 contains material which has a lower vapor pressure at room temperature than the matrix material of the matrix layer 20. The material of the capping layer 60 may or may not absorb the laser beam 4. The thickness of the capping layer 60 is preferably much less than the thickness of the matrix layer 20. The structure of FIG. 5 can then be used as a support for an analyte for MALDI spectroscopy which has a very long shelf life and will last a longer time in the vacuum environment of a mass spectrometer than a pure matrix material layer 20. The capping layer 60 does not itself sublime rapidly at room temperature, and the capping layer 60 prevents the underlying matrix material 20 from rapid sublimation at room temperature.

FIG. 6 shows the structure of FIG. 5 with an analyte layer 50 deposited on the capping layer 60 of FIG. 5. Once again, the layer of analyte material 50 may be pure analyte material, or it may be analyte material plus a matrix material. The matrix material contained in analyte layer 50 may be either the matrix material of the layer 20, or another matrix material.

FIG. 7 shows an innovative structure where the structure of FIG. 4 has a capping layer 60 deposited on top of the analyte layer 50. The capping material 60 contains material which has a lower vapor pressure at room temperature than the matrix material of the matrix layer 20. This arrangement protects the analyte layer 50 and the matrix layer 20 from premature evaporation in the vacuum system of the mass spectrometer.

The structure of FIG. 7 also acts in an innovative way to control the vapor formed when the matrix layer 20 and/or the analyte layer 50 absorbs the laser beam 4. The vapor pressure and the time during which the vapor containing matrix molecules and the analyte molecules are in intimate contact may then be more precisely controlled to control the charge transfer processes which lead to ionized analyte molecules. The number of charged analyte molecules which are counted in the mass spectrometer may then be maximized and/or the conditions optimized for maximum resolution of the analyte in the mass spectrometer. This technique is particularly useful when no matrix molecules are included in the analyte layer 50, as the sensitivity of the MALDI technique is often lowered if the substance to be analyzed is not intimately mixed with the matrix material.

The structure of FIG. 4 may be formed by depositing a layer 50 of analyte material alone (with no matrix material) on to the layer of matrix material 20. The analyte layer 50 and the matrix material may 20 be intermixed by brief heating of the substrate 10 and the two layers 20 and 50. This procedure is more preferable in the case of structure 7, since the structure may be heated to a higher temperature for a longer time without losing too much material to sublimation. The capping layer 60 prevents the loss of material.

The structure of FIG. 4 may be formed by depositing a layer 50 of analyte material alone (with no matrix material)

on to the layer of matrix material 20. The analyte layer and the matrix material may be intermixed by depositing a layer of volatile solvent which dissolves the matrix material of layer 20 on top of analyte layer 50. As long as the amount of volatile solvent is insufficient to dissolve all of the material in layer 20, the solvent will dissolve the matrix material, and as the solvent evaporates, the matrix material will recrystalize on to the seed layer formed by the remnants of matrix layer 20. As the matrix material crystalizes from the solution, the analyte molecules are entrapped in the matrix material and mixed with the matrix material.

The structure of FIG. 4 may also be formed by concurrent deposition of the matrix material and an analyte from a vapor deposition source as sketched in FIG. 3.

Experimental Results

The samples were formed by sublimation onto quartz microscope slides at room temperature. The sublimation vessel 40 was Pyrex held at a source temperature of 70° to 100° C. The samples reached 100 to 600 nm thickness in 1.5 to 10 minutes as controlled by the source temperature. The deposition rate was thus 1 to 2 nm/s. The source-slide distance was either 8 or 10 cm. The flight path was maintained at a technical vacuum of ~$10^{-4}$ torr. Even then, the major component of pressure was sublimated material as these compounds commonly have finite vapor pressures at ambient temperature.

The resultant films were transparent, nearly colorless and displayed negligible optical scattering. High power optical microscopic inspection of the films showed them to be finely polycrystalline on a micron or sub-micron scale. No dichroism was apparent in the UV spectra as checked by tilting the films 45° to the optical path.

Figure 8:
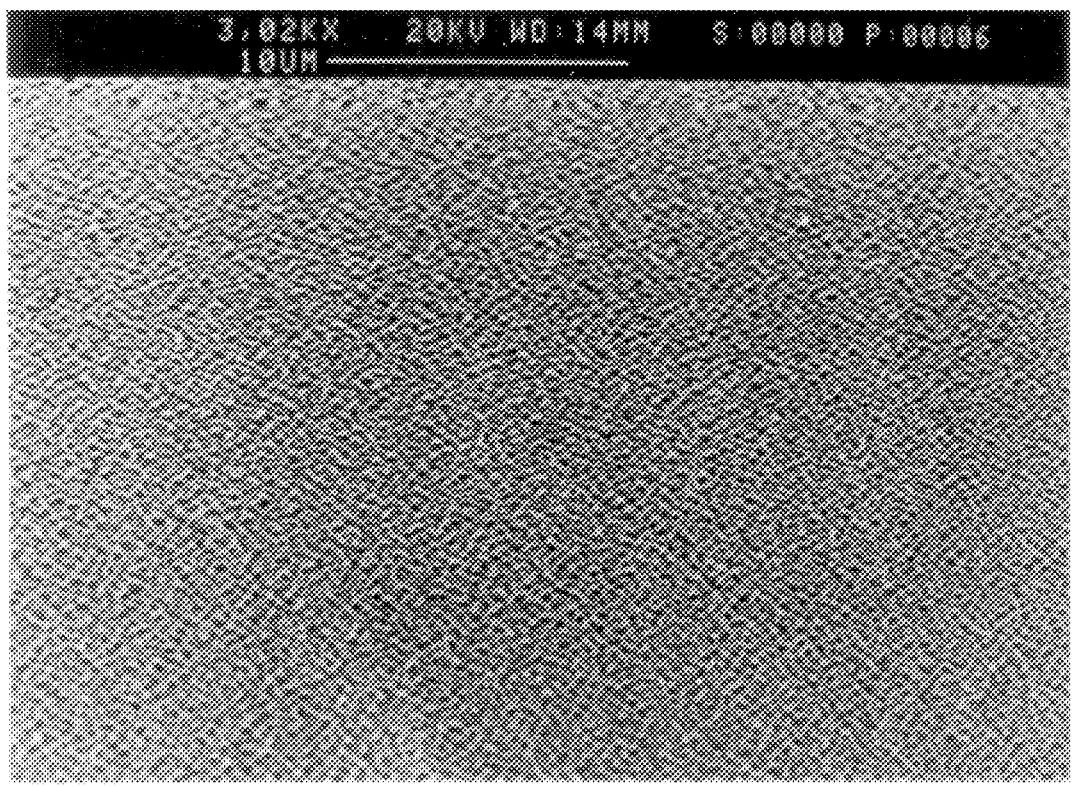
FIG. 8. A Scanning Electron Micrograph of the surface of a layer of matrix material deposited by the method of the invention.

Very thick (~1 micron) coumarin 120 films were examined with a scanning electron microscope (SEM) also. The above crystallites were magnified (see FIG. 8) to show that the micron sized structure was actually the tops of a dense layer of ~2 micron long by ~0.3 micron (=300 nm) diameter facetted columns lying at random angles, see FIG. 8. The surface roughness was estimated to be ~100 nm. I presume that the ratio of roughness to thickness l scales as the square root of thickness; i.e. $l^{1/2}$. Under this assumption thickness and absorptivity will have an estimated experimental uncertainty of ~50 nm (i.e. ~18%) for a 300 nm thickness and ~100 nm or 10% for a 1 micron thickness. Measuring the thickness of the films was critical to establishing the absorptivity. The thickness was measured using a Dektak 3ST profiler. Prior to profiling, small areas (~1 mm$^2$) of the films were removed either with a focused UV laser or mechanical swabbing to produce an observable step in the same area as earlier utilized for the optical transmission measurement. The profiler (2.5 micron dia.) stylus load onto the sample was limited to 1 mg/cm$^2$ as heavier loads scratched the surface. The instrumental accuracy of the thickness measurements was <1 nm and hence negligibly small. No local irregularities in thickness were recorded by the profiler in the area adjacent to the cleared spots, although SEM pictures show the stylus diameter must have rested on the tops of several crystallites. The average uniformity of the film in these areas was thus more uniform than the maximum uniformity estimated above. Uncertainties in establishing the exact mass of material for the optical absorption were a combination of overestimating the thickness of the film due to surface roughness and the possibility that the film was possibly ~90% of theoretical (1.1 g/cm2) density. This density value is near the low end of anticipated densities and chosen to partially compensate for the density not reaching the theoretical maximum.

The UV absorption was determined by an ATI Unicam UV spectrometer operating under ATI Unicam Vision Software V2.11 program for a PC. The wavelength resolution was 1.5 nm; i.e. much less than the width of the observed features. The spectra were commonly run 1 to 3 hours after the preparation of the films.

The magnitude of the absorptivity, $\alpha$, is derived from the sample transmission, T, by the usual formula $$\alpha = -(2.3/l)\log_{10} T \tag{1}$$

where l is the thickness in cm. The $\log_{10} T$ term is recorded directly by the UV spectrometer. The values of peak and 337 nm absorptivity are noted in Table I for a number of MALDI matrices. Also, the maximum optical cross-sections are tabulated and compared to the solution values. The cross-section is calculated assuming a solid density of 1.1 g/cm$^3$ unless more exact information is available.

TABLE 1

| MATRIX | 337 nm $\alpha_{film}$ (cm$^{-1}$) | MAXIMA | | | | |
|---|---|---|---|---|---|---|
| | | $\sigma_{film}$ (cm$^2$) | FWHM$_{film}$ (nm) | $\sigma_{soln}$ (cm$^2$) | FWHM$_{soln}$ (nm) | OS$_{film}$/OS$_{soln}$ |
| Coumarin 120 | 9.69 × 10$^4$ | 3.91 × 10$^{-17}$ | 110 | 7.16 × 10$^{-17}$ | 54 | 1.11 |
| Ferulic Acid | 1.16 × 10$^5$ | 3.46 × 10$^{-17}$ | 81 | 6.10 × 10$^{-17}$ | 70 | 0.66 |
| Sinapinic Acid | 1.10 × 10$^5$ | 4.34 × 10$^{-17}$ | 104 | 6.85 × 10$^{-17}$ | 60 | 1.10 |
| α-CHC | 2.18 × 10$^5$ | 1.04 × 10$^{-16}$ | 89 | 8.24 × 10$^{-17}$ | 59 | 1.90 |
| 2,5-DHB | 7.95 × 10$^4$ | 1.98 × 10$^{-17}$ | 118 | 1.46 × 10$^{-17}$ | 44 | 3.64 |
| Nicotinic Acid* | $\alpha_{248}$ = 7.35 × 10$^4$ $\alpha_{266}$ = 8.71 × 10$^4$ | 1.67 × 10$^{-17}$ | 40 | 1.76 × 10$^{-17}$ | 29 | 1.31 |

I claim:

1. An apparatus for Matrix Assisted Laser Desorption and Ionization (MALDI) Mass Spectrometry comprising;

a substrate; and a first layer deposited on the substrate, the first layer comprising molecules of matrix material, the first layer being substantially free of pinholes, the first layer having an average thickness between 1 nanometer and 10 micrometers.

2. The apparatus of claim 1, where the average thickness is less than 1 micrometer.

3. The apparatus of claim 2, where the average thickness is less than 100 nanometers.

4. The apparatus of claim 1, where the first layer has a thickness variation of less than +/−50% of the average thickness of the first layer.

5. The apparatus of claim 4, where the first layer has a thickness variation of less than +/−10% of the average thickness of the first layer.

6. The apparatus of claim 1, further comprising a second layer deposited on the first layer, the second layer comprising molecules of higher molecular weight than the first layer; and a third layer deposited on the second layer, the third layer comprising material having substantially less vapor pressure than the vapor pressure of the matrix material.

7. The apparatus of claim 1, further comprising a second layer deposited on the first layer, the second layer comprising material having substantially less vapor pressure than the vapor pressure of the matrix material.

* * * * *